(12) United States Patent
Ban

(10) Patent No.: US 6,654,120 B2
(45) Date of Patent: Nov. 25, 2003

(54) SYNOVIAL FLUID CONTROL

(75) Inventor: Robert W. Ban, Redondo Beach, CA (US)

(73) Assignee: Quantimetrix Corporation, Redondo Beach, CA (US)

( * ) Notice: Subject to any disclaimer, the term of this patent is extended or adjusted under 35 U.S.C. 154(b) by 0 days.

(21) Appl. No.: 09/935,811

(22) Filed: Aug. 23, 2001

(65) Prior Publication Data

US 2003/0040036 A1 Feb. 27, 2003

(51) Int. Cl.$^7$ .............................. G01J 4/00; G02B 27/28; G01N 33/53; G01N 33/555
(52) U.S. Cl. ...................... 356/365; 359/494; 435/7.24; 435/7.25
(58) Field of Search ..................... 435/29, 7.25, 7.24; 356/365; 359/494; 372/105

(56) References Cited

PUBLICATIONS

Lenz et al. Needle Biopsy in Gout and Pseudogout (translated title), Beitrage Zur Pathologie, (1976), 157 (2) 161–82, Medline Abstract.*
Weinberger et al. Arch Intern Med, (1981) 141 (9), 1183–7.*

* cited by examiner

Primary Examiner—Christopher R. Tate
Assistant Examiner—Patricia A Patten
(74) Attorney, Agent, or Firm—Maria Erlinda Co Sarno

(57) ABSTRACT

A control reference material for the measurement of cells and crystals that are present in synovial fluid at different pathognomic conditions. Several possible suspending buffers for the control, its methods of preparation and a method for using these controls for analyses are provided. These controls are less costly and more readily available in greater quantities than current controls prepared from normal human synovial fluid as the suspending base.

30 Claims, No Drawings

SYNOVIAL FLUID CONTROL

BACKGROUND

This invention relates to the measurement of cell counts and identification of crystals in synovial fluid samples and more particularly in providing a control reference material for the quality control of the measurements of these cells and the identification of these crystals of interest.

Synovial fluid, often referred to as joint fluid, is a viscous liquid found in joint cavities and supplies nutrients to the cartilages and acts as a lubricant to the surfaces of the frequently moving joints. It is formed as an ultrafiltrate of the plasma across the synovial membranes, into which a mucopolysaccharide containing hyaluronic acid and a small amount of protein is secreted by the cells of the synovial membrane. The chemical composition of the synovial fluid is essentially the same as human plasma except for the high molecular weight proteins which are normally absent in the synovial fluid. It is established that total cell count, differential white blood cell count and crystal identification on synovial fluid can provide valuable information regarding infection, inflammation, and irritation of the joint spaces. Total cell counts are usually performed in a counting chamber, while crystals are analyzed using light and polarized light microscopy. Red blood cells are seen in synovial fluid samples either as a result of a traumatic tap of the joint or as a result of a hemorrhagic condition. Lymphocytes and other white blood cells are seen during conditions of non-septic inflammation while neutrophils are seen during conditions of bacterial sepsis and crystal induced inflammation. Identifying the causative crystals in the synovial fluid, herein also referred to simply as fluid, especially if they are found intracellularly in neutrophils and macrophages, is pathognomic for a crystal induced arthritis. Pathognomic means characteristic of a disease condition or stage.

Gout and pseudogout comprise the two major crystal induced arthritides. The presence of intracellular monosodium urate (MSU, hereinafter) crystals in neutrophils and macrophages is found in 90% of patients having an acute attack of gout. These crystals, however, are also seen in synovial fluid between attacks in 75% of patients, suggesting that multiple factors contribute to an acute episode. Pseudogout, or calcium pyrophosphate deposition disease, is characterized by the presence of calcium salts in cartilage and calcium pyrophosphate dihydrate (CPPD, hereinafter) crystals in synovial fluid. Unlike gout, no single serum metabolite is responsible for the disease. Hereditary metabolic problems or endocrine disorders, such as hypothyroidism and hyperparathyroidism, that elevate calcium levels in blood can lead to pseudogout. More commonly, pseudogout is associated with degenerative arthritis, demonstrated by X-ray evidence of articular cartilage calcification. As many as 50% of adults may have CPPD deposits in their joints at the time of their deaths. Techniques for crystal analysis focus on MSU and CPPD, the two most common crystals. MSU crystals are needle shaped and produce negative birefringence with polarized light. CPPD are often rhomboid, but are also seen as needles and rods, and are weakly birefringent with polarized light, producing positive birefringence. The analyses of these crystals using polarized microscopy and the counting of the cells using counting chambers are known. Other birefringent materials that may also be found in the synovial fluid include calcium oxalate, cartilage fibers, collagen, cholesterol, hydroxyapatite, betamethasone acetate, cortisone acetate, methyl prednisone acetate, prednisone tebulate, triamcinolone acetonide, triamcinolone hexacetonide, EDTA (ethylenediamine tetraacetate), fat or cholesterol esters, lithium heparin, starch granules and debris.

Analysis of synovial fluid is widely accepted as a crucial aid in the evaluation of joint diseases. Identification of crystals in joint fluid establishes a definite diagnosis of these diseases and the leukocyte count can be used to broadly group diseases as inflammatory or noninflammatory. Although these analyses are diagnostically crucial, there is no established available reference control material designed to monitor the accuracy, reliability and reproducibility of these tests or analyses. Incidents of misclassification between inflammatory and noninflammatory due to a wide range of cell count reported are known and discrepancies in crystal identification causing false positives and false negatives have been reported. These affect both diagnosis and treatment. Several factors have been proposed as reasons for these errors such as lack of training and experience with the test methodologies by the laboratory analysts, the infrequency of testing performed in synovial fluids, the differences in the quality and nature of the equipment used for performing the tests, the difference in the diluting fluids used for the specimens, the amount of crystals present in a sample or specimen, differences in the viscosity of the samples, procedural variations in the handling and pipetting of the samples, and differences in time after which a sample or specimen is tested after collection. Clearly, quality control measures are needed for these tests.

It is therefore an object of this invention to provide a reference control material that can be easily prepared in commercial quantity to help improve the reliability of the test results obtained by testing laboratories.

It is also an object of this invention to provide a pathognomic reference control material having red and or white blood cells and or crystals for identifying and differentiating patients with degenerative arthritis from those patients suffering from gout.

It is a further object of this invention to provide several diluent or base materials suitable for suspending cell/s and/or crystals for the reference control material.

SUMMARY OF THE INVENTION

Laboratories have used synovial fluid obtained from the knee of patients with relatively inactive rheumatoid arthritis as a negative control in the analyses of patients' synovial fluids. Others have spiked human synovial fluid with known amounts or either monosodium urate (MSU) or calcium pyrophosphate (CPPD) crystals or a combination of these. However, to use human synovial fluid as a base for the preparation of a reference control material is not practical because of its limited quantity. Further, simply spiking the synovial fluid from a normal individual with the crystals or other birefringent materials of interest do not present a pathognomic reference control material because white blood cells and/or red blood cells may not be present in these spiked samples. This invention offers several synovial fluid reference control materials interchangeably referred to herein as synovial fluid control materials of broad flexibility, variety and usage. For a pathognomic synovial fluid reference control material, hereinafter referred to as pathognomic control, it is most preferred to spike a simulated synovial fluid base. This pathognomic control comprises a desired amount of fixed red blood cells, the desired amount less than 5000 cells/ul (microliter), preferably 30–300 cells/ul; a desired amount of fixed white blood cells, the desired amount less than 10000 cells/ul, preferably 300–1500 cells/ul; a desired amount of calcium pyrophosphate crystals, the desired amount less than 300 mg/l (liter), preferably 150 mg/l; and/or a desired amount of sodium urate crystals, the desired amount less than 300 mg/l (liter), preferably 80 mg/l. Because it is a pathognomic control, not all of the components mentioned above need be present in a single formulation but only those required or present in a particular disease state of interest. A simulated synovial fluid base comprises glucose, sodium lactate, potassium and sodium chloride and a preservative. The simulated synovial fluid base preferably contains hyaluronic acid and most preferably contain human serum albumin. The level of cell counts and crystals may vary based on the apparatus and test procedure used to assay the synovial fluid. The above levels or concentrations given herein are preferred simply because they usually need no further dilution before analyses when the most common apparatus or equipment, a hemacytometer and/or a polarizing microscope is/are used.

A method of preparing the pathognomic control in simulated synovial fluid base comprises the steps of: a) dissolving a known amount of glucose, sodium lactate, potassium chloride, sodium chloride and a preservative in water, preferably deionized or distilled; b) stirring the mixture until all added ingredients are in solution; c) adjusting the pH of the solution to 7.0±1.0, preferably 7.4±0.1; d) adding water to the mixture to a known volume; e) filtering the solution through a 0.2 u membrane; f) dividing the solution into two equal parts; g) adding calcium pyrophosphate crystals, white blood cells, and red blood cells to one part; h) adding sodium urate crystals, white blood cells and red blood cells to the other part; i) rechecking the pH of the solution and readjusting the pH to 7.0±1.0, preferably 7.4±0.1 if necessary; j) testing the resulting solutions for appearance, pH, glucose, lactic acid, white blood cell, red blood cell, calcium pyrophosphate crystals and sodium urate crystals; and, k) filling the resulting solutions in vials when the test results are acceptable. To improve the birefringence of the crystals and render viscosity to the pathognomic control, sodium hyaluronate is also added. Human serum albumin is also preferably added to closely resemble the protein concentration of a human synovial fluid. Sodium hyaluronate or hyaluronic acid sodium salt is preferably added to a final concentration of less than 1%, preferably 0.1% by initially dissolving sodium hyaluronate in water prior to the addition of the other ingredients enumerated in step a) above. Human serum albumin, when preferred, is usually added with the other ingredients of step a) to a final concentration of 2±0.2 g/dl.

While the preferred pathognomic control illustrated above uses a simulated synovial fluid base, it is found that normal saline, a 0.9% sodium chloride solution; water, preferably deionized or distilled; or, any buffer solution unreactive to the crystals and cells, can be used as a suspending base. Normal saline, water and buffer solutions with pH 7.0±1.0 are herein collectively referred to as aqueous base. The aqueous base and the simulated synovial fluid base are collectively referred to herein as suspending base. Typical buffer solutions suitable for use are phosphate buffers, barbiturate/HCl, imidazole/HCl, MOPS [3-(N-morpholino) propanesulfonic acid], N-(2-acetimido)-2-imidoacetic acid, PIPES (1,4-Piperazinediethanesulfonic acid) and the like. The crystals, sodium urate and calcium pyrophosphate, preferably a dihydrate, and the cells, white blood cells and red blood cells, are referred to herein as the main components of interest. The respective cations of urate and pyrophosphate and their levels of hydration, if applicable, may vary so long as their shape and solubility remains the same.

A synovial fluid reference control material or synovial fluid control in a suspending base may contain only one main component of interest or may combine several of these components in a common suspending base without any deleterious effect. These synovial reference control materials may be prepared by simply adding one of the main components or the components of choice in the suspending base. Aside from the main components of interest, reference control materials may be prepared for the other birefringent materials that may be found in the synovial fluids such as calcium oxalate, cartilage fibers, collagen, cholesterol, hydroxyapatite, betamethasone acetate, cortisone acetate, methyl prednisone acetate, prednisone tebulate, triamcinolone acetonide, triamcinolone hexacetonide, EDTA (ethylenediamine tetraacetate), fat or cholesterol esters, lithium heparin, starch granules and debris in a similar manner. An aqueous base is preferred over a simulated synovial fluid base when the cost of preparing the synovial fluid control is a major factor.

DETAILED DESCRIPTION OF THE INVENTION

The normal amount of synovial fluid in the knee cavity is less than 3.5 milliliter (ml). Therefore, it is impractical to prepare a reference control material in a commercial quantity using human synovial fluid as a base. The initial tendency is to formulate a simulated synovial fluid base mimicking the composition of human synovial fluid wherein known amounts of components to be tested can be added which would serve as a control sample. While this is preferred, it was found that equally suitable reference control materials for synovial fluid analyses can be prepared by adding anyone of or any combination of the main components of interest, namely, urate and pyrophosphate crystals, white blood cells and red blood cells, in the following suspending bases such as normal saline (0.9% sodium chloride in water), water preferably deionized or distilled and other buffer preparations such as phosphate buffers, barbiturate/HCl, imidazole/HCl, MOPS [3-(N-morpholino) propanesulfonic acid], N-(2-acetimido)-2-imidoacetic acid, PIPES (1,4-Piperazinediethanesulfonic acid) and the like. This finding is significant because a large volume of synovial fluid reference control material or synovial fluid control can be prepared at a minimal cost. Additionally, it would be just as easy to prepare control materials for the other birefringent materials found in synovial fluid, typical examples of which were enumerated above. The method of preparing these controls has as a main step, the dissolution of any one of or a combination of the main components of interest in a desired suspending base such as water, normal saline, any suitable buffer solution having a pH of 7.0±1.0, preferably at pH 7.4±0.1, or simulated synovial fluid. It is found that adding a combination of some or all of the components together is possible without any deleterious effect. The desired concentration of the component/s to be added to the suspending base is at the discretion of the control manufacturer or the testing laboratory which is usually dictated by the type of equipment or apparatus used for counting the cells and/or the type of equipment or apparatus used for analyzing the presence of the crystals, more particularly its birefringence under polarized light. The typical concentrations which may not require further dilution before analysis are as follows: fixed red blood cells, less than 5000 cells/ul (microliter), preferably 30–300 cells/ul; fixed white blood cells, less than 10000 cells/ul, preferably 300–1500 cells/ul; calcium pyrophosphate crystals, less than 300 mg/l (liter), preferably 150 mg/l; sodium urate crystals, less than 300 mg/l (liter), preferably 80 mg/l.

The ability to suspend the components of interest in an aqueous base was found to be feasible because of the use of fixed white blood cells and fixed red blood cells. Methods of fixing the cells are known and fixed cells are commercially available. The fixed white blood cell and fixed red blood cell used herein come in concentrations of approximately $10^{10}$ cells/liter. The pH of the base is important because extreme pH conditions (below 6 and above 8) may affect the solubility of the urate and pyrophosphate crystals and may also lyse the cells. A preservative is usually added to prevent bacterial contamination. The typical concentrations of preservatives depend upon the type of preservative used and are known in the art. Example A shows a method of preparing a one component synovial fluid control in normal saline.

The synovial fluid control described above can have only one or more of the components of interest. However, one may desire a pathognomic synovial fluid reference material which contains all of the main components at concentration ranges covering those typically found in a particular disease condition or state. For a pathognomic control, the main components may be added to an aqueous base or to a simulated synovial fluid base, which are collectively referred to as suspending base. Example B shows the method of preparing a pathognomic control in normal saline. The pathognomic controls may be prepared separately according to a disease state or combined to serve as control for different disease states. The pathognomic controls illustrated in Examples B and C are prepared separately according to a disease state, identified as Type A and Type B. Type A preferably contains calcium pyrophosphate dihydrate crystals, fixed red blood cells and fixed white blood cells, predominantly, lymphocytes. The Type A control is used primarily to detect patients with degenerative arthritis. Calcium pyrophosphate dihydrate crystals appear as rhomboids, in needle or rod form and are weakly birefringent with polarized light, producing a positive birefringence. The Type B control contains sodium urate, fixed red blood cells and fixed white blood cells, predominantly neutrophils. This reference control material is used to detect patients suffering from gout. Sodium urate appear as needles and produce a negative birefringence with polarized light.

Birefringent materials have the ability to bend or refract light due to the presence of a molecular grain produced by the nonrandom, linear internal structure of the crystals, the grain running down the length of the crystal. This molecular grain causes incident light passing through the crystal to split in two rays: a fast ray which passes with the molecular grain, and a slow ray which passes 90 degrees to the fast ray or against the molecular grain. Whether the birefringence is negative or positive is determined by a formula: $BR=(RI_{\parallel}-RI_{\perp})$. The birefringence is positive if the refractive index parallel to the long axis of the crystal is greater than the refractive index perpendicular to the long axis of the crystal. It is negative if the relationship is reversed.

The preparation of synovial fluid control in an aqueous base has been described above. For a pathognomic synovial control in simulated synovial fluid base, as illustrated in Example C, the crystals and fixed white blood cells together with fixed red blood cells are mixed with the simulated synovial fluid base containing glucose, sodium lactate, potassium chloride, and preferably, sodium hyaluronate. Human serum albumin is also preferably added to the simulated synovial fluid base. To prevent bacterial contamination, a preservative is usually added to the reference control material. The addition of sodium hyaluronate is preferred although not strictly necessary, to impart viscosity. It was observed that a viscosity similar to the natural human synovial fluid improved the birefringence of the crystals under polarized light. For a control reference material containing both hyaluronate and human serum albumin, the composition and preferred levels are as follows: human serum albumin, 1–5%, preferably 2%; hyaluronic acid, 0–1%, preferably 0.1%, calcium pyrophosphate, 0–300 mg/l, preferably 150 mg/l; sodium urate needles, 0–300 mg/l, preferably 80 mg/l; glucose, 00.1%, preferably 0.08%; sodium lactate, 0–0.1%, preferably 0.02%, potassium chloride, 0–1%, preferably 0.03%; sodium chloride 0–1%, preferably 0.6% and a preservative. 0–0.5%, preferably 0.2% sodium azide is sufficient. Other polymers commonly known to impart viscosity can be used instead of hyaluronic acid such as dextran, polyethylene glycol, gelatin, starch, gums, polysaccharides and the like. These polymers, however, unlike hyaluronate, may not improve the birefringence of the crystals.

All the examples herein are mainly provided for illustration and not as a limitation to the invention especially with regards to the different suspending bases, the relative concentrations of the components, i.e. birefringent crystals, white blood cells, red blood cells, the relative amounts of the ingredients in the simulated synovial fluid base and the separation of the pathognomic control according to a disease state.

EXAMPLE A

Preparation of A One Component Synovial Fluid Control

A typical example for a preparation of a 1000 ml of calcium pyrophosphate in normal saline is as follows:

9 grams of sodium chloride and 0.95 grams of sodium azide are dissolved in 900 ml of distilled water. The pH is checked and adjusted to 7.4±0.1 with sodium hydroxide or hydrochloric acid, if needed. 145 mg of calcium pyrophosphate crystals are added without stirring. The volume is then adjusted to 1000 ml and the resulting suspension is placed on a shaker for 2 hours to evenly disperse the crystals. The resulting suspension is assayed for calcium pyrophosphate which will present as rhomboids with weak birefringence.

EXAMPLE B

Preparation of A Pathognomic Control in Aqueous Base

A typical example for the preparation of 1000 ml each of Type A and Type B in an aqueous base is as follows:

Type A is prepared by weighing 9 grams of sodium chloride and 0.95 grams of sodium azide and dissolving these in 900 ml of distilled water. The pH is checked and adjusted to 7.4±0.1 with sodium hydroxide or hydrochloric acid, if needed. One ml of fixed red blood cells and 4.9 ml of fixed white blood cells are added to the saline solution and stirred gently, preferably using a stir plate, for five minutes. 145 mg of calcium pyrophosphate crystals are added without stirring. The volume is then adjusted to 1000 ml and the resulting suspension is placed on a shaker for 2 hours to evenly disperse the crystals. The resulting suspension is assayed for red and white blood cell counts which should fall at 100±20/ul and 500±20/ul, respectively. Calcium pyrophosphate will present as rhomboids with weak birefringence.

Type B is prepared by weighing 9 grams of sodium chloride and 0.95 grams of sodium azide and dissolving these in 900 ml of distilled water. The pH is checked and adjusted to 7.4±0.1 with sodium hydroxide or hydrochloric acid, if needed. Half ml of fixed red blood cells and 9.0 ml of fixed white blood cells are added to the saline solution and stirred gently, preferably using a stir plate, for five minutes. 80 mg of recrystallized sodium urate needles are added without stirring. The volume is then adjusted to 1000 ml and the resulting suspension is placed on a shaker for 2 hours to evenly disperse the crystals. The resulting suspension is assayed for red and white blood cell counts which should fall at 50±5/ul and 1000±50/ul, respectively. Sodium urate will present as needles with strong birefringence.

EXAMPLE C

Preparation of A Pathognomic Control in Simulated Synovial Fluid Base

A typical example for preparing 500 ml. each of a Type A and Type B synovial fluid reference control material is as follows: For a preparation containing hyaluronic acid, weigh one (1) gram of sodium hyaluronate in a container having 900 ml of deionized or distilled water and stir the mixture preferably at 4 degrees Centigrade until the sodium hyaluronate is completely dissolved. To this resulting solution, add the following ingredients, 800 milligram (mg) of glucose, 224.2 mg of sodium lactate, 298.2 mg of potassium chloride, 5.844 grams of sodium chloride. If it is desired to add human serum albumin, dissolve 20 grams into the same mixture. A preservative is recommended to keep the solution from bacterial contamination. One may choose the preservative to add but for sodium azide, for example, addition of 2 grams into the mixture is sufficient. This above mixture is stirred further to ensure complete dissolution. When the ingredients are completely dissolved, the pH of the resulting solution is preferably adjusted to pH 7.4±0.1 with sodium hydroxide or hydrochloric acid. The pH adjusted solution is then transferred to a one liter graduated cylinder or a volumetric flask and diluted to mark with deionized water or distilled water and mixed thoroughly. The resulting solution is then tested for total protein if human serum albumin is added, glucose, and lactic acid. The desired results for this formulation is pH 7.4±0.1; 2.0±0.2 grams/dl protein; 80±5 mg/dl glucose and 2.0±0.2 mmol (millimole)/liter lactic acid. If the results do not fall within these ranges, adjustments are made, respectively. The solution is then filtered through a 0.2 u (micron) filter membrane to reduce bacterial burden. 980 milliliters of the resulting solution is then divided into two portions of 490 milliliters each and are labeled Type A and Type B. To one portion, Type A, add 73.5 milligrams (mg) of calcium pyrophosphate, 2.45 milliliters (ml) of fixed white blood cells and 0.49 ml. of fixed red blood cells. To the Type B portion, add 39.2 mg of sodium urate crystals, 4.9 ml of fixed white blood cells and 245 ul of fixed red blood cells. After addition, the pH is rechecked and pH adjustments are made, if necessary. The Type A and Type B reference control materials are assayed for the white and red blood cell contents and the identity of the crystals are analyzed. For Type A control, the white blood cells should test 500±20/ul; the red blood cells should test 100±10/ul; and it should test positive for calcium pyrophosphate and negative for sodium urate crystal. For Type B control, the white blood cells should test 1000±50/ul; the red blood cells should test 50±5/ul; and it should test positive for sodium urate crystal and negative for calcium pyrophosphate.

All the ingredients used herein are commercially available except for sodium urate which needs further processing. Commercially available sodium urate is usually amorphous and needs to be processed to a crystalline form. The process for transforming amorphous sodium urate to crystalline needles is as follows: a desired amount of amorphous sodium urate is suspended in water, for example a one gram amount can be suspended in approximately 170 ml of water, and boiled under reflux for three (3) hours. The resulting cloudy solution is filtered with a 0.45 u filter and the filtrate is kept at 20–25 degrees centigrade in a stoppered flask. If no crystallization occurs within two days, the solution is seeded with urate crystals obtained from a previous batch.

The availability of a synovial fluid reference control material provides a vehicle for testing the accuracy, precision and reliability of the test equipment or apparatus and the test procedure or method used to detect the components in the synovial fluid. Consequently, this increases the reliability of detecting or diagnosing a pathongomic condition such as those associated with joint disorders, generally classified as noninflammatory, inflammatory, septic, crystal induced and hemorrhagic. This is accomplished by testing the synovial reference control material along with the rest of the samples to ensure that both the control and the samples undergo the same handling conditions. While the test procedures and apparatus vary according to the choice of the analyst or the testing laboratory, the process for monitoring the accuracy, precision and reliability of a synovial fluid test, comprises: a) providing a synovial reference control material having a given range of cell counts and/or characteristics of a crystal by a control manufacturer, the characteristic being a shape, birefringence and the like; b) providing a synovial fluid test apparatus for testing the synovial reference control material and synovial fluid samples; c) performing synovial fluid analyses on the synovial fluid reference control material and the synovial fluid samples; d) comparing the results obtained from the synovial fluid reference control material from step c) with the manufacturer's given range of cell counts and/or characteristics of the crystal in the synovial fluid reference control material; and, e) accepting the results obtained for the synovial fluid samples from step c) when the results of the synovial fluid reference control material obtained from step c) agrees with the manufacturer's given cell count and characteristics of the crystal in the synovial fluid reference control material.

The following illustrates a test employing a synovial fluid reference control material using the most commonly used equipments, a hemacytometer for cell count and a polarizing microscope for characterizing a crystal based on its shape, birefringence and the like, for testing the cell counts and crystal characteristics of a synovial fluid sample usually taken from a patient. The typical steps of the test method are as follows: a) placing a synovial fluid reference control material or a synovial fluid sample having a cell and/or a crystal in both chambers of a hemacytometer, the chamber having square grids for counting; b) putting the hemacytometer under a microscope equipped with a polarizing filter; c) turning on the polarizing filter to detect presence of birefringent crystals and its shape if present; d) counting the cell in a desired number of square grids; e) comparing the shape and birefringence of the crystal in the synovial fluid reference control material obtained in step c) with that stated by a control manufacturer; f) comparing the cell count in the synovial fluid reference control material obtained in step d) with that stated by a control manufacturer; and, g) accepting results obtained for the synovial fluid samples of step a) when the results of the synovial fluid reference control material obtained from steps c) and/or d) agree with the results stated by the control manufacturer. For cell count, the cells may be prestained prior to counting for better visibility.

The variability of cell counts between vials were tested. Eight vials from each type were subjected to duplicate counts and the results showed a coefficient of variation (CV, hereinafter) of 4.6% for Type A and 2.7% for Type B for the white blood cells and 4.8% for Type A and 7.2% for Type B for the red blood cells. The crystals assayed as expected. Cell counts were performed using microscopy with hemocytometer while the crystals were analyzed using polarized microscopy for their respective birefringence.

The above reference control materials can be stored at refrigerated temperatures of 2–8° C. after use for approximately 6 months. The reference control materials should not be frozen as freeze thaw will affect the integrity of the cells and the crystals. Unopened and unused reference control materials are usually stable for 12 months at 2–8° C. or for one month at room temperature or until the expiration date stated on the product label.

While the embodiment of the present invention has been described, it should be understood that various changes, modifications and adaptations may be made therein without departing from the spirit of the invention and the scope of the appended claims. Those skilled in the art will recognize that other and further variations of the values presented herein are possible. The scope of the present invention should be determined by the teachings disclosed herein, the appended claims and their legal equivalents.

I claim:

1. A pathognomic synovial fluid reference control material for the quality control of tests detecting positive birefringent crystal induced joint diseases in a suspending base unreactive to crystal or cell or a combination of crystal and cell, comprising fixed white blood cells and pyrophosphate crystals in a suspending base containing potassium chloride, the suspending base unreactive to crystal or cell or a combination of crystal and cell.

2. The pathognomic synovial fluid reference control material of claim 1 wherein the pathognomic control further comprises less than 5000 cells/ul of fixed red blood cell.

3. The pathognomic synovial fluid reference control material of claim 1 wherein the pathognomic control further comprises less than 300 mg/l urate crystals.

4. The pathognomic synovial fluid reference control material of claim 1 wherein the fixed white blood cell is less than 10000 cells/ul and the pyrophosphate crystal is less than 300 mg/l.

5. The pathognomic synovial fluid reference control material of claim 1 wherein the resulting control material is at pH 7.0±1.0.

6. The pathognomic synovial fluid reference control materials of claim 1 wherein the joint disease is degenerative arthritis.

7. The pathognomic synovial fluid reference control material of claim 1 wherein the pathognomic synovial fluid reference control is a component of a test for a crystal induced joint disease.

8. The pathognomic synovial fluid reference control material of claim 1 wherein the suspending base is a simulated pathognomic synovial fluid further comprising glucose, sodium lactate, potassium chloride and sodium chloride.

9. The pathognomic synovial fluid reference control material of claim 8 wherein the simulated pathognomic synovial fluid is a water solution of 0–0.1% glucose; 0–0.1% of sodium lactate; 0–1% of potassium chloride; and, 0–1% of sodium chloride.

10. The pathognomic synovial fluid reference control material of claim 8 wherein the simulated pathognomic synovial fluid further comprises a preservative.

11. The pathognomic synovial fluid reference control material of claim 8 wherein the simulated pathognomic synovial fluid further comprises a viscosity imparting additive.

12. The pathognomic synovial fluid reference control material of claim 11 wherein the viscosity imparting additive is hyaluronic acid.

13. The pathognomic synovial fluid reference control material of claim 8 wherein the simulated pathognomic synovial fluid further comprises a viscosity imparting additive and human serum albumin.

14. The pathognomic synovial fluid reference control material of claim 8 wherein the simulated pathognomic synovial fluid further comprises human serum albumin.

15. A pathognomic synovial fluid reference control material for the quality control of tests detecting negative birefringent crystal induced joint diseases in a suspending base unreactive to crystal or cell or a combination of crystal and cell, comprising fixed white blood cells and urate crystals in a suspending base containing potassium chloride, the suspending base unreactive to crystal or cell or a combination of crystal and cell.

16. The pathognomic synovial fluid reference control material of claim 15 wherein the pathognomic control further comprises less than 5000 cells/ul of fixed red blood cell.

17. The pathognomic synovial fluid reference control material of claim 15 wherein the pathognomic control further comprises less than 300 mg/l pyrophosphate crystals.

18. The pathognomic synovial fluid reference control material of claim 15 wherein the fixed white blood cell is less than 10000 cells/ul and the urate crystal is less than 300 mg/l.

19. The pathognomic synovial fluid reference control material of claim 15 wherein the resulting control material is at pH 7.0±1.0.

20. The pathognomic synovial fluid reference control materials of claim 15 wherein the joint disease is gout.

21. The pathognomic synovial fluid reference control material of claim 15 wherein the pathognomic synovial fluid reference control is a component of a test for a crystal induced joint disease.

22. The pathognomic synovial fluid reference control material of claim 15 wherein the suspending base is a simulated pathognomic synovial fluid further comprising glucose, sodium lactate and sodium chloride.

23. The pathognomic synovial fluid reference control material of claim 22 wherein the simulated pathognomic synovial fluid is a water solution of 0–0.1% glucose; 0–0.1% of sodium lactate; 0–1% of potassium chloride; and, 0–1% of sodium chloride.

24. The pathognomic synovial fluid reference control material of claim 22 wherein the simulated pathognomic synovial fluid further comprises a preservative.

25. The pathognomic synovial fluid reference control material of claim 22 wherein the simulated pathognomic synovial fluid further comprises a viscosity imparting additive.

26. The pathognomic synovial fluid reference control material of claim 25 wherein the viscosity imparting additive is hyaluronic acid.

27. The pathognomic synovial fluid reference control material of claim 20 wherein the simulated pathognomic synovial fluid further comprises a viscosity imparting additive and human serum albumin.

28. The pathognomic synovial fluid reference control material of claim 22 wherein the simulated pathognomic synovial fluid further comprises human serum albumin.

29. A method of preparing a pathognomic, synovial reference control material at pH 7.0±1.0, comprising: dissolving pyrophosphate crystals and fixed white blood cells in a suspending base containing potassium chloride unreactive to crystals or cell or a combination of crystal and cell.

30. A method of preparing a pathognomic synovial reference control material at pH 7.0±1.0, comprising: dissolving urate crystals and fixed white blood cells in a suspending base containing potassium chloride unreactive to crystals or cell or a combination of crystal and cell.

* * * * *